US006303608B1

(12) United States Patent
Merce-Vidal et al.

(10) Patent No.: US 6,303,608 B1
(45) Date of Patent: Oct. 16, 2001

(54) 2-{4-[4-(4,5-DICHLORO-2-METHYLIMIDAZOL-1-YL)BUTYL]-1-PIPERAZINYL}-5-FLUOROPYRIMIDINE, ITS PREPARATION AND ITS THERAPEUTIC USE

(75) Inventors: Ramon Merce-Vidal; Jordi Frigola-Constansa, both of Barcelone (ES)

(73) Assignee: Laboratorios Del Dr. Esteve, S.A., Barcelone (ES)

( * ) Notice: Subject to any disclaimer, the term of this patent is extended or adjusted under 35 U.S.C. 154(b) by 0 days.

(21) Appl. No.: 09/445,081

(22) PCT Filed: May 28, 1998

(86) PCT No.: PCT/EP98/03190

§ 371 Date: Feb. 29, 2000

§ 102(e) Date: Feb. 29, 2000

(87) PCT Pub. No.: WO98/55476

PCT Pub. Date: Dec. 10, 1998

(30) Foreign Application Priority Data

Jun. 2, 1997 (FR) .................................................. 97 06738

(51) Int. Cl.⁷ ........................ C07D 403/14; A61K 31/496
(52) U.S. Cl. ...................................... 514/252.19; 544/295
(58) Field of Search ......................... 544/295; 514/252.19

(56) References Cited

U.S. PATENT DOCUMENTS

| 5,128,343 | 7/1992 | Pinol et al. ........................... 514/252 |
| 5,227,486 | * 7/1993 | Merce-Vidal et al. ............... 544/295 |
| 5,292,739 | 3/1994 | Merce-Vidal et al. ............... 514/253 |
| 5,382,586 | 1/1995 | Merce-Vidal et al. ............... 514/254 |
| 5,532,234 | 7/1996 | Frigola-Constansa et al. .. 514/224.2 |

FOREIGN PATENT DOCUMENTS

WO 97/21439   6/1997   (EP) .

OTHER PUBLICATIONS

Saxena, *Pharmac. Ther.* vol. 66 pp. 339–368, 1995.*

* cited by examiner

*Primary Examiner*—Emily Bernhardt
(74) *Attorney, Agent, or Firm*—Rockey, Milnamow & Katz, Ltd.

(57) ABSTRACT

2-{4-[4-(4,5-dichloro-2-methylimidazol-1-yl)butyl]-1-piperazinyl}-5-fluoropyrimidine, and its physiologically acceptable salts; pharmaceutical compositions containing these compounds, and a method of treating vertigo, travel sickness, nausea, depression, anxiety, gastric acid secretion, obsessive/compulsive disorders, panic attacks or sleep apnea using these compounds are disclosed.

7 Claims, No Drawings

2-{4-[4-(4,5-DICHLORO-2-METHYLIMIDAZOL-1-YL)BUTYL]-1-PIPERAZINYL}-5-FLUOROPYRIMIDINE, ITS PREPARATION AND ITS THERAPEUTIC USE

This application is an application filed under 35 U.S.C. Sec. 371 as a national stage of international application PCT/FR97/06738, which was filed Jun. 2, 1997.

The present invention relates to the novel compound 2-{4-[4-(4,5-dichloro-2-methylimidazol-1-yl)butyl]-1-piperazinyl}-5-fluoropyrimidine, its preparation and its therapeutic use, its physiologically acceptable salts, the processes for their preparation and their application as medicaments in human and/or veterinary therapeutics, and the pharmaceutical compositions which comprise them.

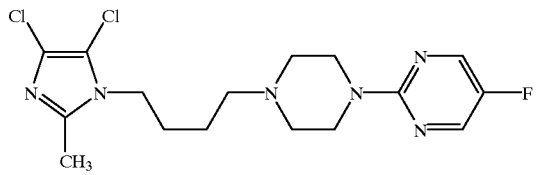

BACKGROUND OF THE INVENTION

Patents EP 382,637 and EP 497,659 of the Applicant Company disclosed various pyrimidinylpiperazinylalkylazole derivatives having anxiolytic and/or tranquilizing properties. Although Patent EP 382,637 claims pyrimidinylpiperazinylalkylazole derivatives substituted at the 5-position of the pyrimidine by a halogen atom, only two examples of compounds of this type are disclosed and, in both cases, it is a bromine atom.

BRIEF SUMMARY OF THE INVENTION

The Applicant Company has now discovered that the introduction of a fluorine atom as substituent at the 5-position of the pyrimidine, in the special case where the azole is an imidazole trisubstituted by a methyl group at the 2-position and by two chlorine atoms at the 4- and 5-positions, gives rise to the compound which is the subject-matter of the present patent, which compound exhibits some advantageous biological properties which make it of particular use in its application in human and/or veterinary therapeutics. In particular, the compound which is the subject-matter of the present patent is of use as an antiemetic against seasickness (nausea caused by motion), as an antidepressant or anxiolytic, as an inhibitor of gastric acid secretion or obsessive-compulsive disorders, in panic attacks and in sleep apnea in mammals, including man.

It is possible to prepare the compound 2-{4-[4-(4,5-dichloro-2-methylimidazol-1-yl)butyl]-1-piperazinyl}-5-fluoropyrimidine and its physiologically acceptable salts according to the invention by one of the processes shown hereinbelow.

a) By reaction of 8-(5-fluoro-2-pyrimidinyl)-8-aza-5-azoniaspiro[4.5]decane with 4,5-dichloro-2-methyl-1H-imidazole in the presence of potassium carbonate and in a dipolar aprotic solvent, such as dimethylformamide. The reaction temperature can vary between 70° C. and the reflux temperature of the solvent, and the reaction time fluctuates between 3 and 48 hours.

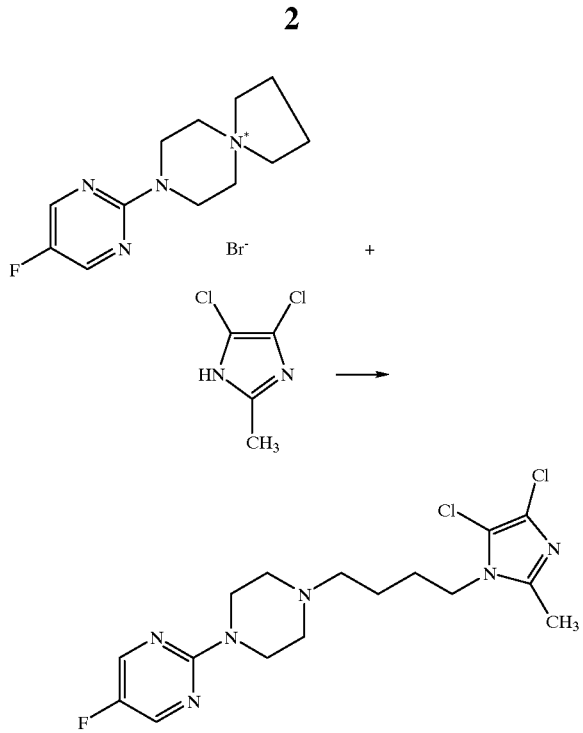

b) By reaction of 5-fluoro-2-(piperazin-1-yl)-pyrimidine with 1-(4-chlorobutyl)-4,5-dichloro-2-methyl-1H-imidazole in the presence of potassium carbonate and in a dipolar aprotic solvent, such as dimethylformamide. The reaction temperature can vary between 70° C. and the reflux temperature of the solvent, and the reaction time varies between 3 and 48 hours. This reaction can also be carried out under phase transfer conditions by using an aqueous sodium hydroxide solution, toluene and a catalyst, such as tetrabutylammonium bromide. Under these conditions, the temperature of the reaction can vary between 50° C. and 90° C., and the reaction time varies between 12 and 72 hours.

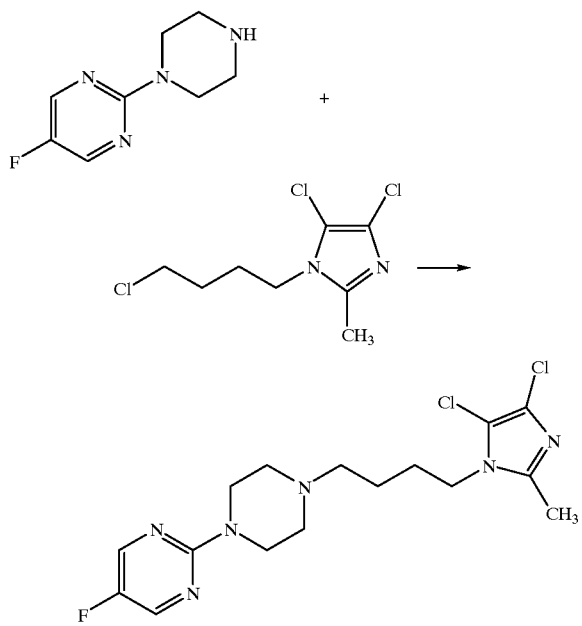

c) By the reaction of 2-{4-[4-(4,5-dichloro-2-methylimidazol-1-yl)butyl]piperazin-1-yl}-5- fluoropyrimidine and of a physiologically acceptable acid, such as citric acid, in a suitable solvent, such as ethanol.

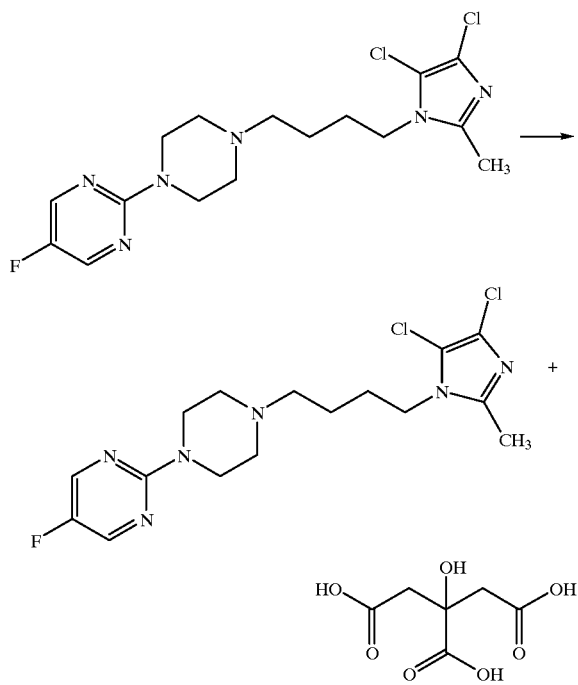

DETAILED DESCRIPTION OF THE INVENTION

The preparation of the novel compound which is the subject-matter of the invention and of its physiologically acceptable salts is shown in the following examples. A description is also given of some biological activities and some forms of use. The examples shown hereinbelow, given simply by way of illustration, must not, however, in any way limit the scope of the invention.

EXAMPLE 1

Preparation of 2-{4-[4-(4,5-dichloro-2-methylimidazol-1-yl)butyl]piperazin-1-yl}-5-fluoropyrimidine A mixture of 3.17 g (0.01 mol) of 8-(5-fluoro-2-pyrimidinyl)-8-aza-5-azoniaspiro[4.5]decane, 2.26 g (0.015 mol) of 4,5-dichloro-2-methyl-1H-imidazole and 76 g (0.02 mol) of potassium carbonate in 80 ml of dimethylformamide is maintained at reflux for 12 hours. The mixture is subsequently evaporated to dryness and the resulting crude product is redissolved in chloroform and washed repeatedly with water. The organic phase is dried and evaporated, and then the resulting crude product is purified by chromatography on a column of silica gel. 3.3 g (85% yield) of 2-{4-[4-(4,5-dichloro-2-methylimidazol-1-yl)butyl]piperazin-1-yl)-5-fluoropyrimidine are obtained in the form of an oil.

IR (film), cm$^{-1}$: 2944, 1610, 1555, 1503, 1449, 1402, 1361, 1243, 786.

$^1$H NMR (CDCl$_3$, 300 MHz), δ: 1.54 (m, 2H), 1.73 (m, 2H), 2.34 (s, 3H), 2.38 (m, 2H), 2.43 (m, 4H), 3.74 (m, 4H), 3.85 (m, 2H), 8.15 (s, 2H).

EXAMPLE 2

Preparation of 2-{4-[4-(4,5-dichloro-2-methylimidazol-1-yl)butyl]piperazin-1-yl}-5-fluoropyrimidine A mixture of 3.5 g (0.02 mol) of 5-fluoro-2-(piperazin-1-yl)pyrimidine, 6.04 g (0.025 mol) of 1-(4-chlorobutyl)-4,5-dichloro-2-methyl-1H-imidazole and 4.14 g (0.03 mol) of potassium carbonate in 200 ml of dimethylformamide is maintained at reflux for 12 hours. The mixture is subsequently evaporated to dryness and the resulting crude product is redissolved in chloroform and washed repeatedly with water. The organic phase is dried and evaporated, and then the resulting crude product is purified by chromatography on a column of silica gel. 6.4 g (83% yield) of 2-{4-[4-(4,5-dichloro-2-methylimidazol-1-yl)butyl]-piperazin-1-yl}-5-fluoropyrimidine are obtained in the form of an oil.

IR (film), cm$^{-1}$: 2944, 1610, 1555, 1503, 1449, 1402, 1361, 1243, 786.

$^1$H NMR (CDCl$_3$, 300 MHz), δ: 1.54 (m, 2H), 1.73 (m, 2H), 2.34 (s, 3H), 2.38 (m, 2H), 2.43 (m, 4H), 3.74 (m, 4H), 3.85 (m, 2H), 8.15 (s, 2H).

EXAMPLE 3

Preparation of 2-{4-[4-(4,5-dichloro-2-methylimidazol-1-yl)butyl]piperazin-1-yl}-5-fluoropyrimidine citrate 1.1 g (5.2 mmol) of citric acid monohydrate are added to a solution of 2 g (5.2 mol) of 2-(4-[4-(4,5-dichloro-2-methylimidazol-1-yl)butyl]piperazin-1-yl)-5-fluoropyrimidine in absolute ethanol. After a certain period of time, 2.72 g (91% yield) of 2-{4-[4-(4,5-dichloro-2-methylimidazol-1-yl)butyl]piperazin-1-yl}-5-fluoropyrimidine citrate precipitate in the form of a solid with an M.p. of 151–153° C.

IR (KBr), cm$^{-1}$: 3780–2270 (bb), 1707, 1616, 1482, 1429, 1375, 1244, 1214.

$^1$H NMR (d$_6$-DMSO, 300 MHz), δ: 1.53 (m, 2H), 1.66 (m, 2H), 2.33 (s, 3H), 2.53–2.74 (c.a., 10H), 3.75 (m, 4H), 3.94 (t, J=7.2 Hz, 2H), 8.46 (s, 2H).

Antiemetic Activity

The compounds obtained in the invention are studied with regard to their effects on nausea in ferrets according to a method described by Costall et al. (*Neuropharmacology*, 1986, 25, 959–961).

Ferrets of both sexes (0.7–1.4 kg) are individually housed at 21±1° C. and fed normally. The compound of the example or a vehicle is subsequently administered to them subcutaneously as pretreatment 15 minutes before the administration of copper sulfate (CuSO$_4$·5H$_2$O; 100 mg/kg by the intragastric route) or cisplatin (10 mg/kg i.v. by means of a permanent jugular cannula). The animals are observed at the beginning of vomiting and then for 30 minutes (copper sulfate) or 240 minutes (cisplatin). Vomiting is characterized by rhythmic abdominal contractions, either associated with the expulsion of solid or liquid matter (vomit) or not associated with the passage of matter via the mouth (nausea). The number of episodes and nausea or vomiting are recorded.

The compound of Example 3 is capable of altering the nausea induced by copper sulfate and of opposing the nausea induced by cisplatin.

| Compound | Dose (mg/kg s.c.) | Number of episodes of nausea/vomiting |
|---|---|---|
| a) Copper sulfate | | |
| Vehicle | — | 8.2 ± 1.4 |
| Example 3 | 0.001 | 7.4 ± 1.2 (NS) |

-continued

| Compound | Dose (mg/kg s.c.) | Number of episodes of nausea/vomiting |
|---|---|---|
| | 0.01 | 3.2 ± 0.6 (*) |
| | 0.1 | 1.0 ± 0.2 (*) |
| | 1 | 1.7 ± 0.3 (*) |
| b) Cisplatin | | |
| Vehicle | — | 14.2 ± 1.9 |
| Example 3 | 0.001 | 13.8 ± 2.4 (NS) |
| | 0.01 | 6.5 ± 3.1 (*) |
| | 0.1 | 3.1 ± 2.9 (*) |
| | 1 | 3.0 ± 2.0 (*) |

(*) $p < 0.05$ compared with the values of the control vehicle

Study of Travel Sickness in the Shrew (*Suncus murinus*)

The compound of Example 3 is studied with regard to its effect on travel sickness (vertigo) induced in *Suncus murinus* according to the method described by N. Matsuki et al. ("Mechanisms and Control of Emesis", John Libbey Emotex, 1992, 233, 323–329).

Males of the species *Suncus murinus* weighing 58–72 grams are housed in groups of 3 and are allowed free access to solid food and to water. One hour before the test, they are presented with cat food in their housing cage. At the beginning of the test, the animals receive the treatment with the test product by the i.p. route. After 30 minutes, they are placed individually in the test boxes (15×15×10 cm). The boxes are connected to a motor which displaces them over several wheels forward and backward with a frequency which induces nausea in them (travel sickness). This frequency is 1 hertz with an amplitude of displacement of 4 cm. The animals are left in the test boxes for 30 minutes, in order for them to become used to their surroundings, and then the active movement of the cages is begun for 20 minutes, in order to determine the presence or the absence of nausea (without passage of matter from the digestive tract) and of vomiting (with passage of matter from the digestive tract).

The compound of Example 3 markedly inhibits the nausea caused by the movement (travel sickness), reducing both nausea and vomiting, between doses of 0.01 and 10 mg/kg by the i.p. route.

| Compound | Dose (mg/kg i.p.) | Number of episodes of nausea/vomiting |
|---|---|---|
| Vehicle | — | 10.0 ± 1.39 |
| Example 3 | 0.001 | 8.38 ± 1.41 (NS) |
| | 0.01 | 0.33 ± 0.21 (*) |
| | 0.1 | 2.17 ± 0.83 (*) |
| | 1.0 | 0.33 ± 0.21 (*) |
| | 10.0 | 0 ± 0 (*) |

(*) $p < 0.0001$ compared with the values of the control vehicle

Anxiolytic and Antidepressant Activity

The anxiolytic and antidepressant activity is demonstrated by the affinity which the novel compounds exhibit for $5HT_{1A}$ serotonin receptors (D. A. Glitz, *Drugs*, 1991, 41, 11) and by means of the conditioned avoidance response test (J. S. New et al., *J. Med. Chem.*, 1986, 29, 1476).

a) Binding to the $5HT_{1A}$ serotonin receptor

A rat hippocampus homogenate is used, a modification of the method of S. J. Peroutka (Neurochem., 1986, 47, 529) being followed. [$^3$H]-8-HO-DPAT is used as radioligand and serotonin is used to measure the nonspecific binding. The incubation time is 15 minutes at a temperature of 37° C. The radioligand bonded to the protein is separated by filtration through glass fiber filters and the radioactivity retained on the filter is determined by liquid scintillation. The inhibition constant ($K_i$, nM) is calculated by nonlinear regression analysis using the EBDA/LIGAND program (Munson and Rodbard, *Analytical Biochemistry*, 1980, 107, 220).

Compound of Example 3 $K_i$=19.4 nM b) Test of conditioned avoidance response (C.A.R.)

In this test, use is made of male Wistar rats weighing 200 g trained to leap a barrier in a Letica shuttle box (references LI 910 and LI 2700) during the 30 seconds which follow their introduction into the box.

Products having an anxiolytic or tranquilizing activity suppress the conditioned avoidance response.

Training: first day, 11 tests at intervals of 3 minutes. Electric shock in the paws at 30 seconds (5 mA, 0.1 s, 10 s). Second and third days: two daily tests, only with the selected rats {some of the grades of the first day (except the first test)>14}. Day of the test: groups formed by the selected rats. Oral administration of the product or vehicle 45 minutes before the beginning of the study.

Compound of Example 3 $ED_{50}$=9.7 mg/kg, p.o.

Inhibitory Activity with Regard to Gastric Acid Secretion

This activity is determined by means of the Shay procedure (H. Shay et al., *Gastroenterology*, 1945, 5, 43; Visscher et al., *J. Pharmac. Exp. Ther.*, 1954, 110, 188).

Male Wistar rats weighing from 200 to 250 g are used in this test, which rats are deprived of food up to the day preceding the test, with free access to water. Batches of 4 animals each are used, at least.

The rats are anesthetized with ethyl ether, a laparotomy is performed on them and their pylori are tied, and then an abdominal incision is made. The products are administered intraduodenally (i.d.) before suturing the abdominal incision. The dose administered in the first test is 40 mg/kg and then the median effective dose ($ED_{50}$) is determined. The vehicle used is gum arabic at 5% w/v in doubly-distilled water.

Two hours after ligating the pylori, the rats are sacrificed by prolonged anesthesia with ethyl ether and the volume of gastric juice is measured. The total acidity is determined by means of a pH meter equipped with an automatic burette. For each product and for each dose tested, the percentage of inhibition of gastric acid secretion is determined with respect to a reference batch.

Compound of Example 3 $ED_{50}$=1.9 mg/kg, i.d.

The daily dosage in human or veterinary medicine is between 1 mg and 500 mg of product, which may be administered in one or more dispensations. The compositions are prepared in forms which are compatible with the administration route used, such as, for example, tablets, dragees, hard gelatin capsules, suppositories, solutions or suspensions. These compositions are prepared by means of known processes and they comprise from 1 to 60% by weight of the active principle and from 40 to 99% by weight of appropriate pharmaceutical vehicle compatible with the active principle and the physical form of the composition which is appropriate. By way of example, the formulae of three pharmaceutical dosage forms which comprise a product of the invention are presented.

| Example of a tablet formulation | |
|---|---|
| Example 3 | 5 mg |
| Lactose | 60 mg |
| Crystalline cellulose | 25 mg |

| -continued | |
|---|---|
| Povidone K 90 | 5 mg |
| Pregelatinized starch | 3 mg |
| Colloidal silicon dioxide | 1 mg |
| Magnesium stearate | 1 mg |
| Total weight | 100 mg |

Example of a hard gelatin capsule formulation

| Example 3 | 10 mg |
|---|---|
| Polyoxyethylene glyceride | 135 mg |
| Glycerol behenate | 5 mg |
| Excipient | 150 mg |

Example of an injectable preparation formulation

| Example 3 | 4 mg | 8 mg |
|---|---|---|
| Sodium chloride | 15 mg | 30 mg |
| Water for injections q.s. for | 2 ml | 4 ml |

What is claimed is:

1. 2-{4-[4-(4,5-dichloro-2-methylimidazol-1-yl)butyl]-1-piperazinyl}-5-fluoropyrimidine, and its physiologically acceptable salts, of formula

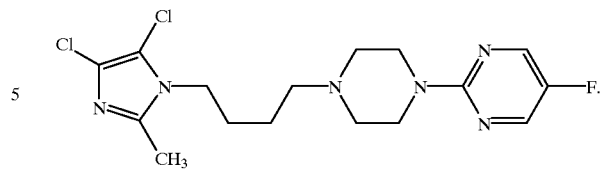

2. 2-{4-[4-(4,5-dichloro-2-methylimidazol-1-yl)butyl] piperazin-1-yl}-5-fluoropyrimidine citrate.

3. A method for the preparation of the compounds of claim 1 comprising the step of
reacting 8-(5-fluoro-2-pyrimidinyl)-8-aza-5-azoniaspiro decane bromide salt with 4,5-dichloro-2-methyl-1H-imidazole in the presence of potassium carbonate in a dipolar aprotic solvent.

4. A method of treating vertigo, travel sickness, nausea, depression, anxiety, gastric acid secretion, obsessive/compulsive disorders, panic attacks, emesis or sleep apnea comprising administering to said mammal a therapeutically effective amount of a compound of claim 1.

5. A pharmaceutical composition comprising a pharmaceutically acceptable vehicle and a compound of claim 1.

6. The method of claim 3 wherein said step is reacting 8-(5-fluoro-2-pyrimidinyl)-8-aza-5-azoniaspiro decane salt with 4,5-dichloro-2-methyl-1H-imidazole in the presence of potassium carbonate in a dipolar aprotic solvent,
wherein reaction temperature varies between 70° C. and the reflux temperature of said solvent and reaction time varies between 3 and 48 hours.

7. The method of claim 6, wherein said dipolar aprotic solvent is dimethylformamide.

* * * * *

UNITED STATES PATENT AND TRADEMARK OFFICE
CERTIFICATE OF CORRECTION

PATENT NO. : 6,303,608 B1
DATED : October 16, 2001
INVENTOR(S) : Merce-Vidal et al.

It is certified that error appears in the above-identified patent and that said Letters Patent is hereby corrected as shown below:

Column 1,
Line 9, please insert sub-title -- FIELD OF THE INVENTION --.

Column 4,
Line 24, please delete "2-(4-[4-(4,5-dichloro-2-methylimidazol-l-yl)butyl]piperazin-l-yl}-5-fluropyrimidine" and insert -- 2-{4-[4-(4,5-dichloro-2-methylimidazol-l-yl)butyl]piperazin-1-yl}-5-fluropyrimidine --

Column 7,
Line 32, please insert a colon after formula

Signed and Sealed this

Eleventh Day of June, 2002

Attest:

JAMES E. ROGAN
Attesting Officer
Director of the United States Patent and Trademark Office